(12) United States Patent
Tokieda et al.

(10) Patent No.: US 9,039,970 B2
(45) Date of Patent: *May 26, 2015

(54) AUTOMATIC ANALYZER

(75) Inventors: Hitoshi Tokieda, Hitachinaka (JP); Isao Yamazaki, Ryugasaki (JP); Masaaki Hanawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 354 days.

This patent is subject to a terminal disclaimer.

(21) Appl. No.: 13/288,332

(22) Filed: Nov. 3, 2011

(65) Prior Publication Data

US 2012/0070343 A1    Mar. 22, 2012

Related U.S. Application Data

(63) Continuation of application No. 11/221,837, filed on Sep. 9, 2005, now Pat. No. 8,071,025.

(30) Foreign Application Priority Data

Sep. 17, 2004    (JP) .................................. 2004-270658

(51) Int. Cl.
  *G01N 35/00*  (2006.01)
  *G01N 35/10*  (2006.01)
  *G01N 35/04*  (2006.01)

(52) U.S. Cl.
  CPC .......... *G01N 35/109* (2013.01); *G01N 35/1065* (2013.01); *Y10T 436/11* (2013.01); *G01N 35/0099* (2013.01); *G01N 2035/0443* (2013.01); *G01N 2035/0444* (2013.01); *G01N 2035/0455* (2013.01); *G01N 2035/1093* (2013.01)

(58) Field of Classification Search
  USPC .......................................................... 422/64
  See application file for complete search history.

(56) References Cited

U.S. PATENT DOCUMENTS

| | | | |
|---|---|---|---|
| 3,728,227 A | 4/1973 | Elson et al. | |
| 4,141,954 A | 2/1979 | Shigetomi | |
| 4,234,538 A | 11/1980 | Ginsberg et al. | |
| 4,276,051 A | 6/1981 | Ginsberg et al. | |
| 4,501,164 A | 2/1985 | Stockdale et al. | |
| 4,774,055 A | 9/1988 | Wakatake et al. | |
| 4,808,380 A | 2/1989 | Minekane | |
| 5,051,238 A | 9/1991 | Umetsu et al. | |
| 5,183,638 A | 2/1993 | Wakatake | |
| 5,305,650 A * | 4/1994 | Koike et al. | 73/864.21 |
| 5,445,037 A | 8/1995 | Itoh | |
| 5,501,984 A * | 3/1996 | Hofstetter et al. | 436/518 |
| 6,019,945 A | 2/2000 | Ohishi et al. | |
| 6,098,484 A | 8/2000 | Bacchi et al. | |
| 2004/0105783 A1 | 6/2004 | Yamazaki et al. | |

FOREIGN PATENT DOCUMENTS

| | | |
|---|---|---|
| JP | 57-90162 A | 6/1982 |
| JP | 2-99868 A | 4/1990 |
| JP | 5-10957 A | 1/1993 |
| JP | 2004-45112 A | 2/2004 |
| WO | 02/068964 A1 | 9/2002 |

* cited by examiner

*Primary Examiner* — Jill Warden
*Assistant Examiner* — Benjamin Whatley
(74) *Attorney, Agent, or Firm* — Mattingly & Malur, P.C.

(57) ABSTRACT

An automatic analyzer having reagent disks disposed inside and outside a reaction disk. A plurality of reagent probes are alternately accessed one by one to each of the reagent disks per cycle. Each reagent probe comprises two arms rotatable independently of each other so that the reagent probe is able to access a plurality of points and interference between the plurality of reagent probes can be avoided. A first reagent and a second reagent can be loaded on each of the reagent disks.

6 Claims, 9 Drawing Sheets

AUTOMATIC ANALYZER

This application is a continuation of U.S. patent application Ser. No. 11/221,837, filed Sep. 9, 2005, now allowed, the contents of which are hereby incorporated by reference into this application.

BACKGROUND OF THE INVENTION

1. Field of the Invention

The present invention relates to an automatic analyzer for automatically analyzing various components of blood, etc., and more particularly to an automatic analyzer capable of loading a larger number of reagents and realizing a higher throughput per unit time.

2. Description of the Related Art

An automatic analyzer for automatically analyzing living samples, such as blood, and outputting analysis results is essential for carrying out analysis with high efficiency in, e.g., large-, medium- and small-scaled hospitals handling a large number of patients, as well as in a clinic center carrying out analysis under contract with those hospitals and doctor's offices.

In that type of automatic analyzer, it is demanded that the system is more compact, is able to perform more kinds of analysis, and has a higher processing speed. To satisfy those demands, various types of automatic analyzers have been proposed so far. For example, Patent Document 1; JP,A 5-10957 discloses an automatic analyzer comprising two reagent disks capable of loading reagents in concentric arrangement, and reagent probes independently movable corresponding to concentric rows of reagent containers. In other words, Patent Document 1 is intended to increase the number of loadable reagents by arranging two reagent disks in concentric relation, and to avoid a reduction of the processing speed by providing reagent probes to be independently movable corresponding to respective rows of reagent containers.

With that disclosed related art, however, because a plurality of reagent probes accessing the row of reagent containers on one reagent disk are operated to rotate about the same rotary shaft, reagents sucked from reagent containers on the same reagent disk can be dispensed just into a reaction cuvette located on the same dispensing position on a reaction disk. Also, reagents sucked from reagent containers on the different reagent disks can be dispensed only to respective positions on the reaction disk different from each other. Thus, analysis cannot be performed at a high speed in random combinations.

To overcome such a problem, Patent Document 2; JP,A 2004-45112 discloses an automatic analyzer including a reagent dispensing probe and provided with a mechanism capable of reciprocally moving the probe not only along a rail interconnecting a plurality of reagent disks, but also in a direction perpendicular to the rail. In other words, Patent Document 2 is intended to enlarge an area where the reagent dispensing probe is movable, thereby widening an area allowing reagent containers and reaction cuvettes to be accessible therein and increasing the degree of freedom in dispensing operations. Further, the processing speed is increased by providing a plurality of reagent dispensing probes which are reciprocally movable along the rail or providing a plurality of rails.

SUMMARY OF THE INVENTION

With the related art disclosed in Patent Document 2, however, since the rail must be laid to extend over the area where the reagent dispensing probe is movable, a frame for supporting the rail is necessary and the frame is required to have a high mechanical strength.

In particular, when a high processing speed is required, a plurality of reagent dispensing probes are disposed and a plurality of rails are provided on the frame. Then, the plurality of the reagent dispensing probes are operated at high speeds at the same time. This gives rise to a problem that vibrations generated especially at start and stop of the operation are propagated to other reagent dispensing probes through the rails, thus resulting in scattering of the reagent, a reduction of dispensing accuracy, and other troubles.

To suppress the generated vibrations, the mechanical strength of the frame must be increased, but an increase of the mechanical strength gives rise to another problem of increasing the frame size. Usually, the mechanical strength of the frame is low when the frame is supported in a cantilevered manner, and is increased by connecting frame members into a box-like structure. However, because the frame is disposed to so as bridge the plurality of reagent disks and the reaction disk loading the reaction cuvettes on it, the frame having a box-like shape is arranged in covering relation to the reagent disks, and operations of replacing reagents set on the reagent disks are very difficult to carry out. In a system with a high processing capability, reagents are consumed at high rates and the frequency of replacing the reagents is increased. For that reason, a difficulty in the operations of replacing reagents is a serious problem.

Also, with the structure in which the reagent dispensing probe is disposed on the rail, the rail length must be prolonged in proportion to enlargement of the area where the reagent dispensing probe is movable, thus resulting in the increased cost.

Further, even in the case providing a plurality of reagent dispensing probes, there occurs a problem that, for example, when two reagent dispensing probes are operated so as to simultaneously access two positions close to each other, only one reagent dispensing probe can be operated in practice because the rails mutually obstruct the respective probe operations.

With the view of overcoming the problems mentioned above, the present invention is constituted as follows.

In an automatic analyzer comprising a reagent disk on which a plurality of reagent containers are arranged along a circumference, a reaction disk on which a plurality of reaction cuvettes are arranged along a circumference, and a mechanism for causing reactions between reagents contained in the reagent containers and samples in the reaction cuvettes and analyzing the reactions developed in the reaction cuvettes, the automatic analyzer includes a plurality of reagent disks and a reagent dispensing probe for sucking the reagent from the reagent container and ejecting the sucked reagent into the reaction cuvette, the reagent dispensing probe comprising a first arm operated to rotate about a first rotary shaft and a second arm operated to rotate about a second rotary shaft disposed on the first arm, the first arm and the second arm being rotatable independently of each other. With those features, the reagent dispensing probe is able to access a wider area, any obstacle such as a support structure is not present above the reagent disks, and maintenance operations such as reagent replacement can be facilitated. The reagent dispensing probe comprising the first arm and the second arm, which are rotatable independently of each other, may be disposed in plural for the purpose of obtaining an even higher processing capability. In this case, since the plurality of reagent dispensing probes can be independently mounted in the automatic analyzer, stable dispensing performance can be ensured without suffering from adverse influences such as reagent scattering and a reduction of the dispensing performance caused by vibrations generated with operations of one or more other reagent dispensing probes.

Also, the area accessible by the reagent dispensing probe is given as an area within the radius of rotation of the second arm about a point on a path along which the center of rotation of the second arm rotates, the center of rotation of the second arm being located in the first arm. Therefore, the area accessible by the reagent dispensing probe can be easily set depending on applications by changing respective lengths of the first arm and the second arm.

Further, in the case operating a plurality of reagent dispensing probes, even when the probes are required to access places close to each other, interference between those probes can be avoided by shifting the operation timings of the first arm and the second arm of the probe. As a result, the dispensing performance can be maximally utilized without being restricted by operations of the other mechanism components unlike the above-described related art using rails.

Thus, according to the present invention, two reaction disks each loading a first reagent and a second reagent thereon are disposed, and either reagent is sucked by only one reagent dispensing probe from either reagent disk per cycle. The reagent dispensing probe is made up two arms rotatable independently of each other so that one probe is able to access a plurality of points and interference between a plurality of reagent dispensing probes can be avoided. Consequently, it is possible to provide an automatic analyzer capable of loading a larger number of reagents and having a higher processing capability per unit time.

DESCRIPTION OF THE PREFERRED EMBODIMENTS

Figure 1:
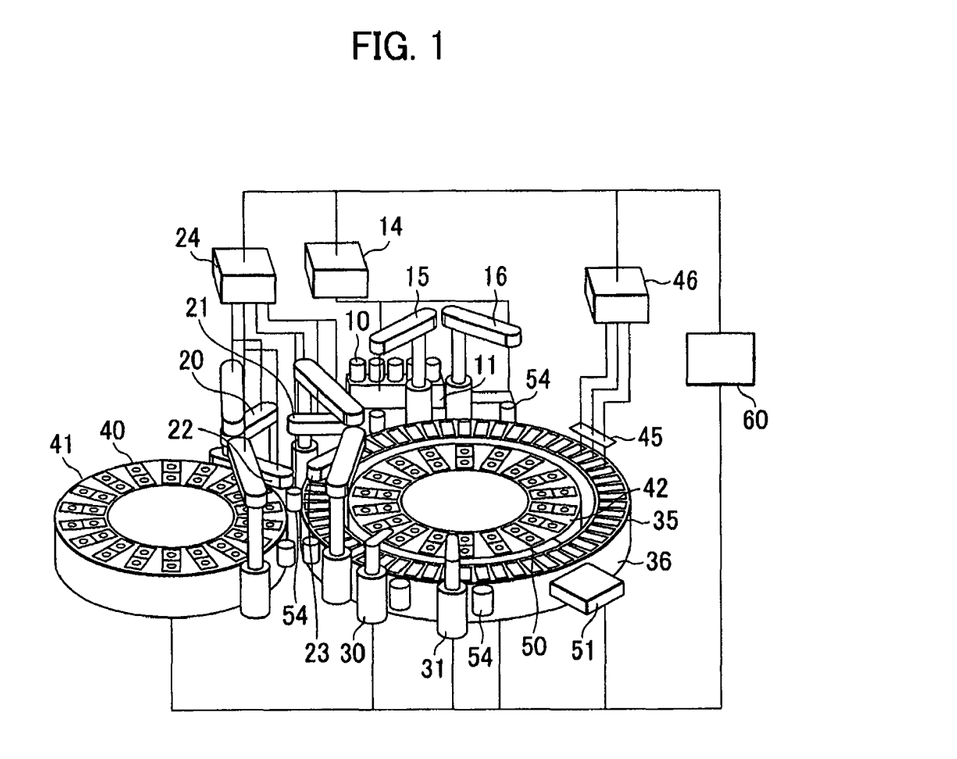
FIG. 1 is a perspective view of an automatic analyzer according to a first embodiment.
Figure 2:
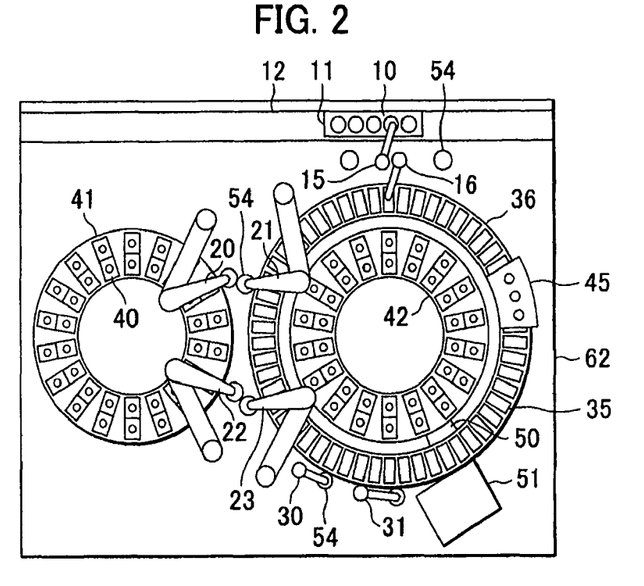
FIG. 2 is a plan view of the automatic analyzer according to the first embodiment.

Embodiments of the present invention will be described below with reference to the drawings. FIGS. 1 and 2 are respectively a perspective view and a plan view of an automatic analyzer according to a first embodiment of the present invention.

A total number 54 of reaction cuvettes 35 are arranged on a reaction disk 36 along its circumference, the reaction disk 36 being disposed on a casing 62. A reagent disk 42 is disposed inside the reaction disk 36, and a reagent disk 41 is disposed outside the reaction disk 36. A plurality of reagent containers 40 are loadable on each of the reagent disks 41, 42 along its circumference. One reagent container 40 contains two kinds of reagents. A conveyer mechanism 12 for moving a rack 11 with sample containers 10 loaded thereon is installed near the reaction disk 36. Reagent (dispensing) probes 20, 21, 22 and 23 are disposed between the reagent disk 41 and the reagent disk 42 to be rotatable in respective planes and movable in the vertical direction. The detailed construction of each reagent probe will be described later.

The reagent probes 20, 21, 22 and 23 are each connected to a reagent pump 24. Between the reaction disk 36 loading the reaction cuvettes 35 thereon and the conveyer mechanism 12, sample probes 15, 16 are disposed to be rotatable in respective planes and movable in the vertical direction. The sample probes 15, 16 are each connected to a sample pump 14. Around the reaction disk 36, there are arranged mixing units 30, 31, a light source 50, an optical detector 51, and a cuvette washing mechanism 45. The cuvette washing mechanism 45 is connected to a washing pump 46.

Washing ports 54 are disposed within respective areas where the sample probes 15, 16, the reagent probes 20, 21, 22 and 23, and the mixing units 30, 31 are movable.

The sample pump 14, the reagent pump 24, the washing pump 46, the optical detector 51, the reaction disk 36 loading the reaction cuvettes 35 thereon, the reagent disk 41, the reagent probes 20, 21, 22 and 23, and the sample probes 15, 16 are each connected to a controller 60.

Figure 3:
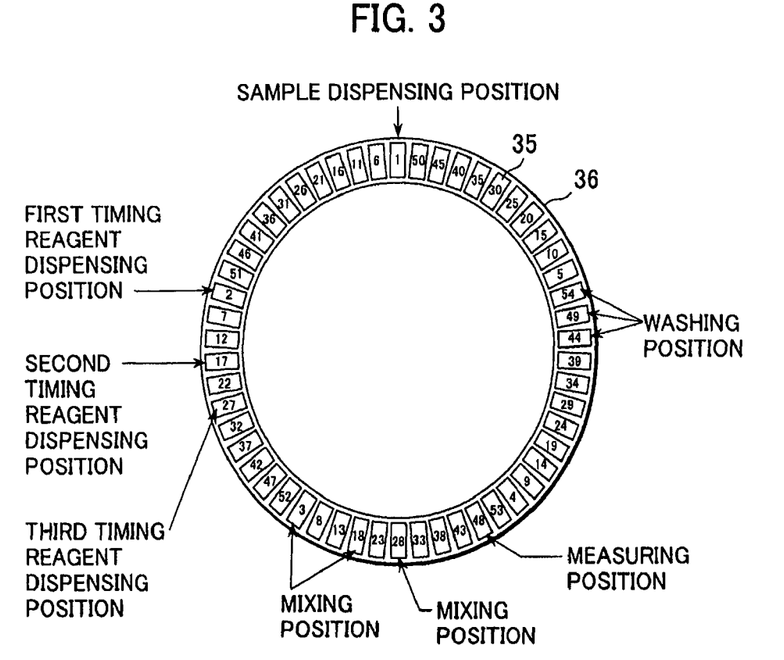
FIG. 3 is an explanatory view of a principal part of the first embodiment.

As shown in FIG. 3, a sample dispensing position, a first timing reagent dispensing position, a second timing reagent dispensing position, a third timing reagent dispensing position, mixing positions, a measuring position, and washing positions are decided along a circumference of the reaction disk 36. Also, the reaction disk 36 is operated to rotate counterclockwise in each stroke of 11 pitches and to stop per preset unit cycle time in a repeated way. In other words, the reaction cuvette located at a position 1 in a certain cycle is advanced to a position 2 in a next cycle.

Figure 4A:
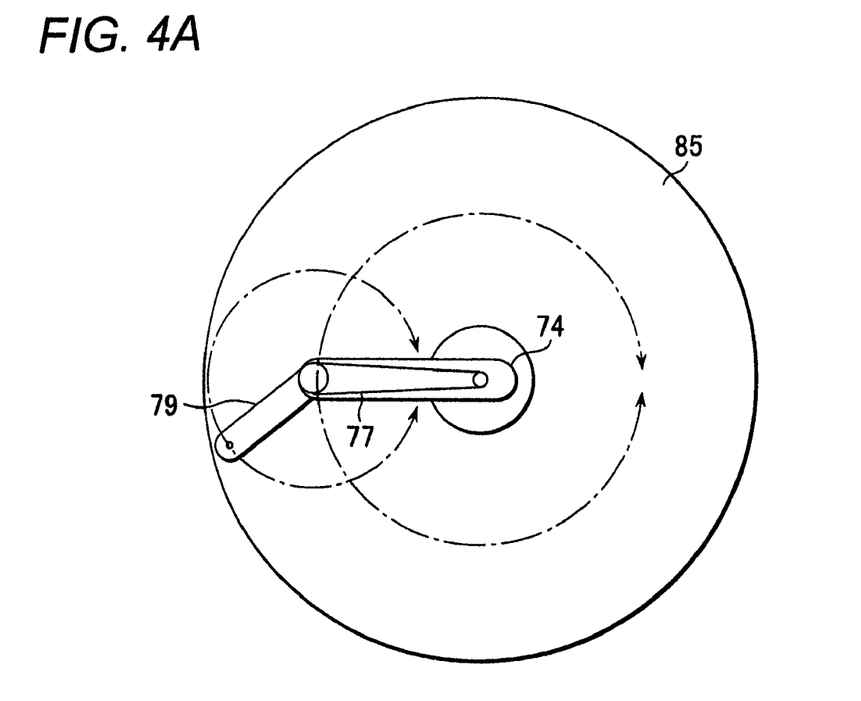
FIG. 4A is a top view and 4B is a plan view showing the construction of a reagent dispensing probe in the first embodiment.
Figure 4B:
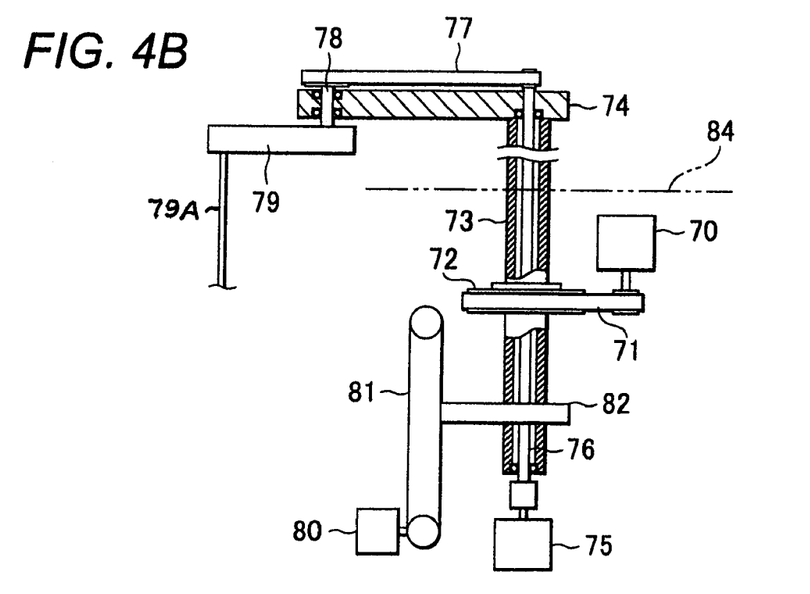

FIGS. 4A and 4B show one example of the construction of the reagent dispensing probe in the first embodiment of the present invention.

The reagent dispensing probe is operated in combination of probe operations in the horizontal direction and the vertical direction. The operation in the horizontal direction is performed in combination of rotations of a first arm 74 and a second arm 79.

The first arm 74 is rotated in such a manner that a rotation drive force of a first arm driving motor 70 is transmitted to a pulley 72 through a belt 71 and then transmitted to the first arm 74 through a hollow shaft 73 coupled to the pulley 72.

The second arm 79 is rotated in such a manner that a rotation drive force of a second arm driving motor 75 is transmitted to a shaft 76 which is directly coupled to a shaft of the motor 75 and is disposed to extend through the hollow shaft 73, and then transmitted through a belt 77 to a shaft 78 which is disposed to penetrate the first arm 74 and serves as a center of the rotation of the second arm 79.

Arm vertical movements are performed as follows. The rotation of a vertical operation driving motor 80 is converted to a linear motion through combination of a pulley and a belt 81. A slider 82 is fixed at its one end to the belt 81 and coupled at its other end to the shaft 73. As a result, the first and second arms are vertically moved at the same time.

An area accessible by the reagent dispensing probe is represented by a circular area 85.

Figure 5:
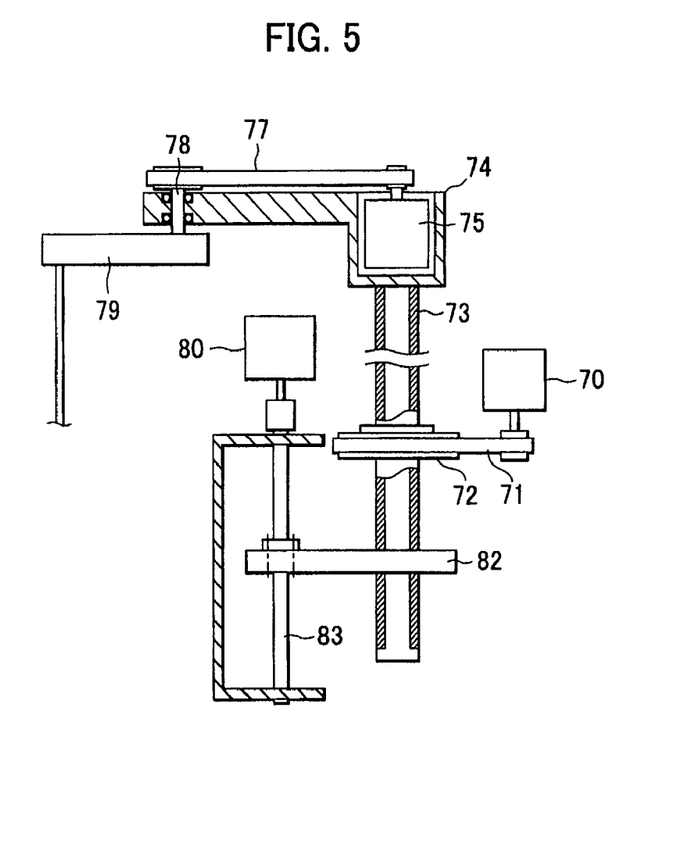
FIG. 5 is a schematic view showing the construction of a reagent dispensing probe in a second embodiment.

FIG. 5 shows another example of the construction of the reagent dispensing probe in a second embodiment of the present invention.

The first arm 74 is rotated in the same manner as described above, while the second arm 79 is rotated by a second arm driving motor 75 disposed inside the first arm 74. Further, arm vertical movements are performed such that a ball screw 83 directly coupled to the vertical operation driving motor 80 converts the motor rotation to a linear motion, and a slider 82 coupled to a nut of the ball screw 83 is vertically moved. Although the shaft 73 is not always required to be hollow in this example, it is preferably hollow from the viewpoint of weight reduction.

The example shown in FIGS. 4A and 4B is advantageous in that, because the motors 70, 75 and 80 are all disposed below an upper surface 84 of a table cover housing the automatic analyzer therein, wiring for the motors 70, 75 and 80 is laid below the upper surface 84 of the table cover and a neat external appearance is obtained. On the other hand, the example shown in FIG. 5 is advantageous in that, because the second arm driving motor 75 is disposed inside the first arm 74 and the shaft 76 shown in FIG. 4B can be dispensed with, the number of necessary parts is cut and the weight of vertically moving parts is reduced, thus resulting in a smaller torque required for the vertical operation driving motor 80.

Though not shown, the second arm driving motor 75 may be disposed at a top of the shaft 78 about which the second arm 79 is rotated, and may be directly connected to the shaft 78. In this case, the belt 77 is no longer required and the number of necessary parts can be further cut.

Using the automatic analyzer thus constructed, the analysis is performed in the sequence described below.

Figure 6:
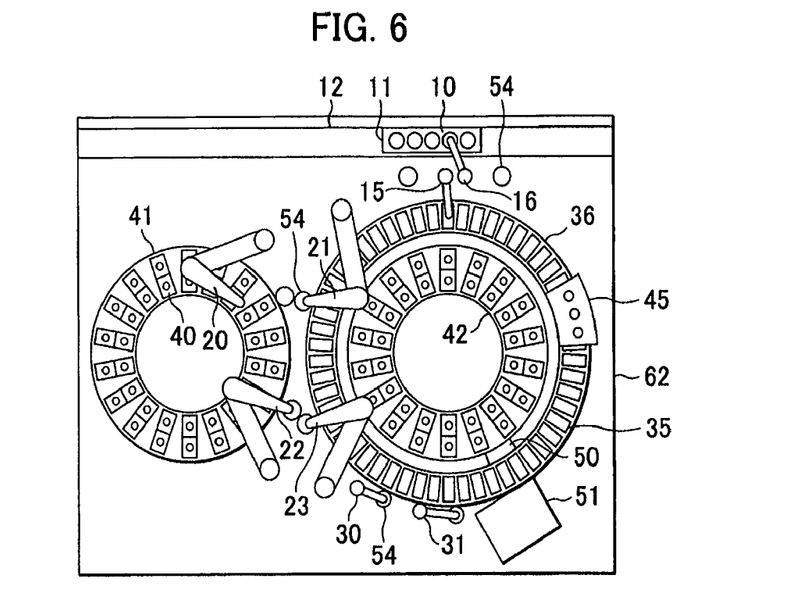
FIG. 6 is an explanatory view for explaining the operation of the automatic analyzer according to the first embodiment.

A sample to be analyzed, such as blood, is put in the sample container 10. The sample container 10 is placed on the rack 11 and then conveyed by the conveyer mechanism 12. Thereafter, the sample probe 15 sucks a sample in amount required for a first test from one of the sample containers 10 located at a particular position (FIG. 2). Then, in a first cycle, a predetermined amount of the sample is ejected from the sample probe 15 into one reaction cuvette 35 located at a position 1 (FIG. 3) on the reaction disk 36. During that period, the reagent probe 20 sucks a predetermined amount of a first reagent corresponding to the first test from one of the reagent container 40 loaded on the reagent disk 41 (FIG. 6).

Figure 7:
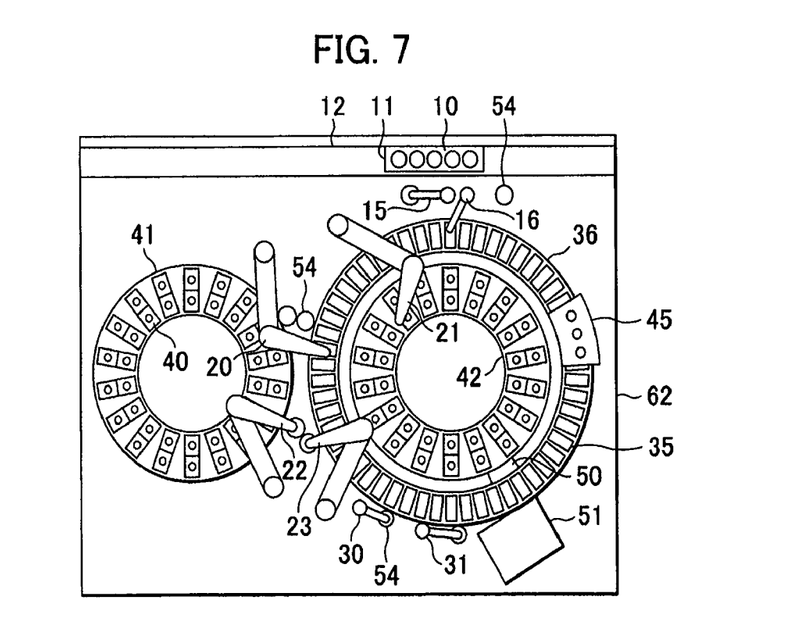
FIG. 7 is an explanatory view for explaining the operation of the automatic analyzer according to the first embodiment.

In a second cycle, the relevant reaction cuvette is advanced to a position 2 on the reaction disk 36. At that position 2, the reagent probe 20 ejects the predetermined amount of the first reagent into the relevant reaction cuvette. During that period, the sample probe 15 is washed (FIG. 7).

Figure 8:
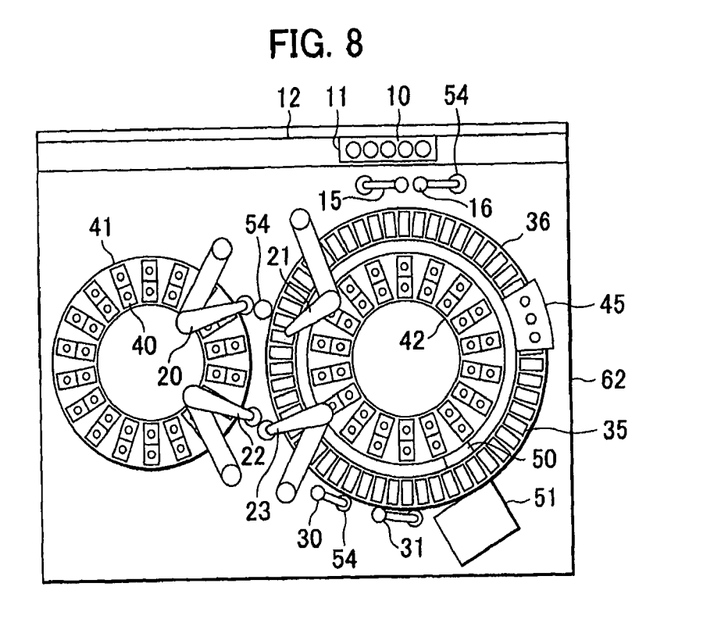
FIG. 8 is an explanatory view for explaining the operation of the automatic analyzer according to the first embodiment.

In a third cycle, the reagent and the sample in the relevant reaction cuvette are mixed by the mixing unit 30 at a position 3 on the reaction disk 36. During that period, the reagent probe 20 is washed (FIG. 8).

Figure 9:
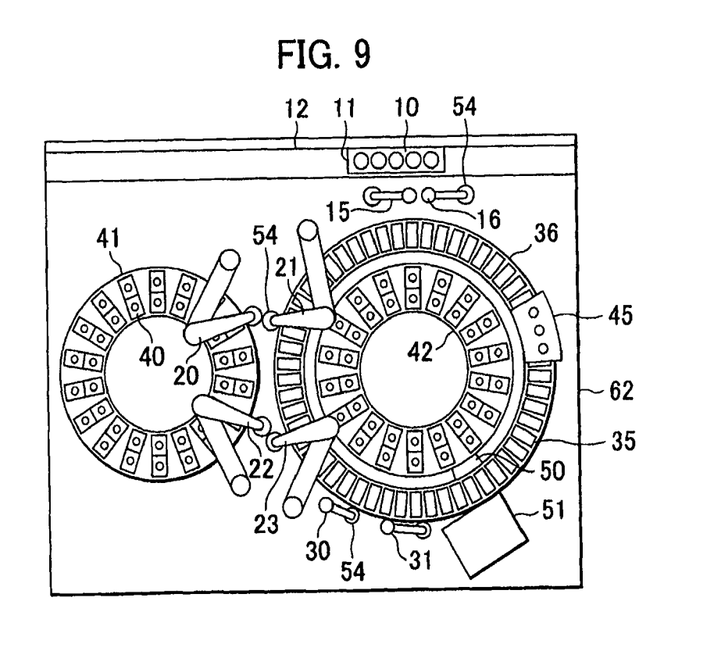
FIG. 9 is an explanatory view for explaining the operation of the automatic analyzer according to the first embodiment.

In a fourth cycle, while the relevant reaction cuvette is rotated to a position 4 on the reaction disk 36, it passes between the light source 50 and the optical detector 51 so that optical measurement is carried out. During the rotation of the reaction disk 36, the mixing unit 30 is washed in the washing port 54 (FIG. 9).

In each of ninth, 14th, 19th, 24th, 29th, 34th and 39th cycles, the optical measurement is carried out in a similar manner.

Figure 10:
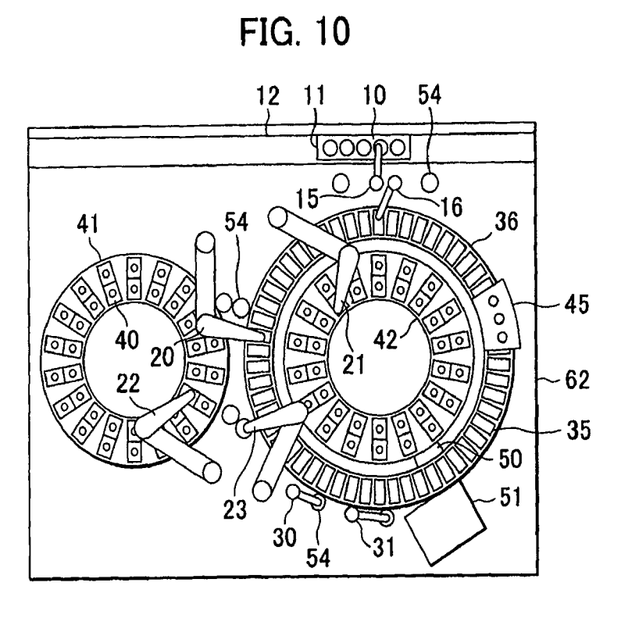
FIG. 10 is an explanatory view for explaining the operation of the automatic analyzer according to the first embodiment.
Figure 11:
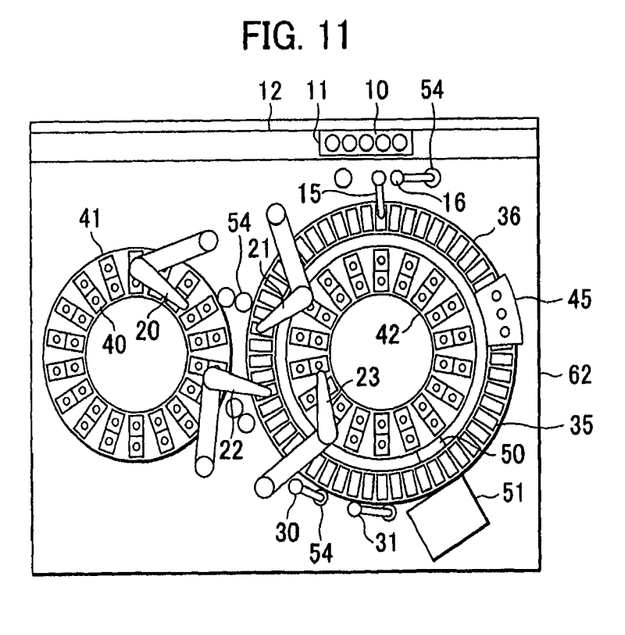
FIG. 11 is an explanatory view for explaining the operation of the automatic analyzer according to the first embodiment.
Figure 12:
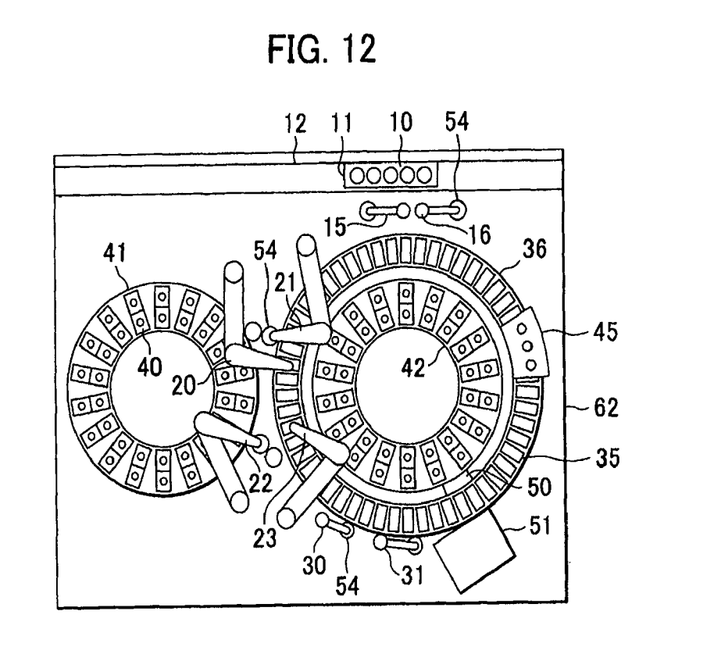
FIG. 12 is an explanatory view for explaining the operation of the automatic analyzer according to the first embodiment.

When the first test requires a second reagent to be dispensed at the second timing, the reagent probe 22 sucks, in a 16th cycle, the second reagent from one of the reagent containers 40 loaded on the reagent disk 41 (FIG. 10) and then ejects, in a 17th cycle, the second reagent into the relevant reaction cuvette located at a position 17 on the reaction disk 36 (FIG. 11). In an 18th cycle, the mixing unit 31 mixes the liquid in the relevant reaction cuvette located at a position 18 on the reaction disk 36. During that period, the reagent probe 22 is washed (FIG. 12).

When the first test requires the second reagent to be dispensed at the third timing, the reagent probe 22 sucks, in a 26th cycle, the second reagent from one of the reagent containers 40 loaded on the reagent disk 41 and then ejects, in a 27th cycle, the second reagent into the relevant reaction cuvette located at a position 27 on the reaction disk 36. In a 28th cycle, the mixing unit 31 mixes the liquid in the relevant reaction cuvette located at a position 28 on the reaction disk 36. During that period, the reagent probe 22 is washed.

After dispensing the second reagent, mixing the liquid and repeating the optical measurement, the cuvette washing mechanism 45 sucks the liquid in the relevant reaction cuvette and then pours a washing liquid into the relevant reaction cuvette at a position 44 or 49 on the reaction disk 36 in a 44th or 49th cycle. Further, the washing liquid is completely sucked in a 54th cycle.

Results of the optical measurements performed plural times using the optical detector 51 are sent to the controller 60 in which concentrations of items to be measured in the first test are calculated.

A second test is performed as follows. In a first cycle, the sample probe 16 sucks a sample in amount required for the second test from the sample container 10 located at a particular position (FIG. 6). Then, in a second cycle, a predetermined amount of the sample is ejected from the sample probe 16 into one reaction cuvette 35 located at the position 1 on the reaction disk 36. During that period, the reagent probe 21 sucks a predetermined amount of a first reagent corresponding to the second test from one of the reagent containers 40 loaded on the reagent disk 42 (FIG. 7).

In a third cycle, the relevant reaction cuvette is advanced to the position 2 on the reaction disk 36. At that position 2, the reagent probe 21 ejects the predetermined amount of the first reagent into the relevant reaction cuvette. During that period, the sample probe 16 is washed (FIG. 8).

In a fourth cycle, the reagent and the sample in the relevant reaction cuvette are mixed by the mixing unit 30 at the position 3 on the reaction disk 36. During that period, the reagent probe 21 is washed (FIG. 9).

In a fifth cycle, while the relevant reaction cuvette is rotated to the position 4 on the reaction disk 36, it passes between the light source 50 and the optical detector 51 so that optical measurement is carried out. During the rotation of the reaction disk 36, the mixing unit 30 is washed in the washing port 54.

In each of tenth, 15th, 20th, 25th, 30th, 35th and 40th cycles, the optical measurement is carried out in a similar manner.

When the second test requires a second reagent to be dispensed at the second timing, the reagent probe 23 sucks, in a 17th cycle, the second reagent from one of the reagent container 40 loaded on the reagent disk 42 (FIG. 11) and then ejects, in an 18th cycle, the second reagent into the relevant reaction cuvette located at a position 18 on the reaction disk 36 (FIG. 12). In a 19th cycle, the mixing unit 31 mixes the liquid in the relevant reaction cuvette located at the position 18 on the reaction disk 36. During that period, the reagent probe 23 is washed (FIG. 9).

When the second test requires the second reagent to be dispensed at the third timing, the reagent probe 23 sucks, in a 27th cycle, the second reagent from one of the reagent container 40 loaded on the reagent disk 42 and then ejects, in a 28th cycle, the second reagent into the relevant reaction cuvette located at the position 27 on the reaction disk 36. In a 29th cycle, the mixing unit 31 mixes the liquid in the relevant reaction cuvette located at the position 28 on the reaction disk 36. During that period, the reagent probe 23 is washed.

After dispensing the second reagent, mixing the liquid and repeating the optical measurement, the cuvette washing mechanism 45 sucks the liquid in the relevant reaction cuvette and then pours a washing liquid into the relevant reaction cuvette at the position 44 or 49 on the reaction disk 36 in a 45th or 50th cycle. Further, the washing liquid is completely sucked in a 55th cycle.

Results of the optical measurements performed plural times using the optical detector 51 are sent to the controller 60 in which concentrations of items to be measured in the second test are calculated.

In a third test, the same steps as those in the first test are repeated with a delay of 2 cycles. In a fourth test, the same steps as those in the second test are repeated with a delay of 2 cycles. Thereafter, those two types of test sequences are successively repeated through similar steps, whereby concentrations of items to be measured for the sample are analyzed with a plurality of tests.

Thus, with this embodiment, the reagent probe 20 accesses the reagent disk 41 to suck the reagent from it in an odd-numbered cycle, and the reagent probe 22 accesses the reagent disk 41 to suck the reagent from it in an even-numbered cycle. Therefore, those two probes are avoided from simultaneously accessing the reagent disk 41 in the same cycle. Likewise, the reagent probe 23 accesses the reagent disk 42 to suck the reagent from it in an odd-numbered cycle, and the reagent probe 21 accesses the reagent disk 42 to suck the reagent from it in an even-numbered cycle. Therefore, those two probes are avoided from simultaneously accessing the reagent disk 41 in the same cycle. As a result, it is possible to shorten the cycle time and to increase the number of samples analyzable in a certain time.

Also, since only one reagent probe sucks the reagent from the corresponding reagent disk during one cycle, a time for sucking the sample and a time for moving the probe can be prolonged, and the reagent can be stably dispensed with high accuracy.

Further, since two reagent disks are independently rotatable and only one reagent probe sucks the reagent from the corresponding reagent disk in one cycle, combinations of reagents to be sucked for the same test can be freely selected and analysis can be realized with a high processing capability while being adapted for irregular combination of analysis items.

Moreover, with this embodiment, the first and second reagents used in each odd-numbered test are both sucked from the reagent disk 41, and the first and second reagents used in each even-numbered test are both sucked from the reagent disk 42. Stated another way, the first and second reagents used for the same analysis item can be put on the same reagent disk in one side. Thus, since the reagents for each analysis item are replaced with respect to the corresponding reagent disk in either side, a time and labor required for replacing the reagents can be cut and errors in the replacing operations can be reduced.

With this embodiment, two kinds of reagents can be put in the reagent container 40. Therefore, the first reagent and the second reagent for use in one analysis item can be put in one reagent container 40, thus allowing the first reagent and the second reagent to be replaced at a time. As a result, a time and labor required for replacing the reagents can be cut and errors in the replacing operations can be reduced.

With this embodiment, since the reagent probe 20 accesses the first timing reagent dispensing position on the reaction disk 36 in an even-numbered cycle and the reagent probe 21 accesses it in an odd-numbered cycle for ejecting the first reagent, those two probes are avoided from simultaneously accessing the first timing reagent dispensing position in one cycle. Likewise, since the reagent probe 22 accesses the second or third timing reagent dispensing position on the reaction disk 36 in an odd-numbered cycle and the reagent probe 23 accesses it in an even-numbered cycle for ejecting the second reagent, those two probes are avoided from simultaneously accessing the second or third timing reagent dispensing position in one cycle. Also, since the first timing reagent dispensing position, the second timing reagent dispensing position, and the third timing reagent dispensing position are located away from each other, the probes are able to access those positions at the same time. This means that just one period for ejecting the reagent is required in each cycle. As a result, it is possible to shorten the cycle time and to increase the number of samples analyzable in a certain time.

In addition, since only one probe ejects the reagent at the same position in one cycle, a time required for ejecting the reagent can be prolonged and the reagent can be ejected with high accuracy and high reproducibility. Accordingly, the reagent can be dispensed in an accurate amount, and the analysis can be performed with high accuracy.

With this embodiment, the reagent probes 20 and 23 suck the reagents in odd-numbered cycles and eject the reagents in even-numbered cycles, while the reagent probes 21 and 22 suck the reagents in even-numbered cycles and eject the reagents in odd-numbered cycles. Therefore, each probe is just required to perform the steps of sucking the reagent, ejecting the sucked reagent, and washing itself during a time of two cycles. As a result, the operation time can be set with a sufficient margin, and stable operation can be ensured.

Still further, since a longer operation time is set for each reagent probe, a range over which the probe is movable can be increased and the size of the reagent disk can be enlarged correspondingly. Therefore, more kinds of reagents required for analyses can be loaded on one reagent disk at the same time.

With this embodiment, since the eject position of the reagent probe 20 and the eject position of the reagent probe 21 are matched with each other, the reagents can be dispensed at equivalent timing regardless of from which one of the probes the first reagent is ejected. Accordingly, the reaction process can be analyzed under identical conditions.

With this embodiment, since the reagent probes 22 and 23 can access the second timing reagent dispensing position and the third timing reagent dispensing position in common to eject the second reagent, it is possible to analyze plural kinds of reactions in which the second reagent is mixed at different timings, and to increase the number of kinds of analyzable items.

Furthermore, since the eject positions are in common between the reagent probes 22 and 23, the analysis can be performed under identical conditions.

Since the reagent disk 41 and the reagent disk 42 are disposed respectively outside and inside the reaction disk 36 with the reagent eject positions on the reaction disk located between them, those two reagent disks can be installed at a shorter distance therebetween.

Also, since the reagent disks 41 and 42 are installed close to each other, the distance to each of the common reagent eject positions is shortened and so is the distance over which the reagent probe is moved. It is hence possible to shorten the cycle time and to increase the number of samples analyzable in a certain time.

With this embodiment, since the sample probes 15 and 16 alternately repeat the steps of sucking the sample and ejecting it, only one sample probe accesses either the sample container 10 or the reaction cuvette 35. It is hence possible to shorten the cycle time and to increase the number of samples analyzable in a certain time.

Further, since the sample probes 15 and 16 are each just required to perform the steps of sucking the sample, ejecting the sucked sample, and washing itself during two cycles, the operation time for dispensing and probe movement can be set with a sufficient margin. As a result, the reagent can be dispensed in a higher accurate amount, and the analysis can be performed with higher accuracy.

With this embodiment, in a test using a sample dispensed by the sample probe 15, a first reagent is dispensed by the reagent probe 20 from the reagent disk 41, and a second reagent is dispensed by the reagent probe 22 from the reagent disk 41. In a test using a sample dispensed by the sample probe 16, a first reagent is dispensed by the reagent probe 21 from the reagent disk 42, and a second reagent is dispensed by the reagent probe 23 from the reagent disk 42. Accordingly, the sample probe 15, the reagent disk 41, the reagent probe 20, and the reagent probe 22 constitute a first set, while the sample probe 16, the reagent disk 42, the reagent probe 21, and the reagent probe 23 constitute a second set. These sets are independent of each other such that one of the sets is in no way combined with the other. Therefore, calibration using the sample probe 15, the reagent probe 20 and the reagent probe 22 is just required for each of the analysis items corresponding to the reagents loaded on the reagent disk 41, and calibration using the sample probe 16, the reagent probe 21 and the reagent probe 23 is just required for each of the analysis items corresponding to the reagents loaded on the reagent disk 42. Thus, since only the calibration is required for each set, it is possible to reduce the number of calibrations to be performed, to avoid wasteful use of the reagents and time, and to eliminate differences in analysis results caused by different characteristics among the probes.

If the first timing of reagent dispensing is shifted from the second or third timing of reagent dispensing by even-numbered cycles, there is a possibility that the first reagent and the second reagent must be sucked from the same reagent disk in one cycle. In contrast, according to this embodiment, the first timing of reagent dispensing is shifted from the second or third timing of reagent dispensing by odd-numbered cycles, the first reagent being sucked from one reagent disk, the second reagent being sucked form the other reagent disk, the first reagent and the second reagent being alternately sucked with each other.

Mores specifically, with this embodiment, since a total number 54 of reaction cuvettes 35 are loaded and each reaction cuvette is rotated in stroke of 11 pitches per cycle, the reaction cuvette is rotated over 1 rotation plus 1 pitch in five cycles. Therefore, one reaction cuvette located at a certain position on the reaction disk is moved to a position adjacent to the certain position, i.e., a position shifted 1 pitch from it, after 5 cycles. If the reaction cuvette is rotated over 1 rotation plus 1 pitch in even-numbered cycles, one reaction cuvette located at a certain position on the reaction disk is moved to a position adjacent to the certain position, i.e., a position shifted 1 pitch from it, after the even-numbered cycles. In this case, the reaction cuvette is moved to one of successive positions in turn at a time difference corresponding to the even-numbered cycles. If it is attempted in such a case to separately perform the timing of dispensing the first reagent and the timing of dispensing the second reagent respectively in an even-numbered cycle and an odd-numbered cycle, the eject positions of the first reagent and the second reagent are located apart away from each other, and the reagent probes must be installed in positions apart away from each other correspondingly. In contrast, according to this embodiment, since the reaction cuvette is rotated over 1 rotation plus 1 pitch in odd-numbered cycles, the eject positions of the first reagent and the second reagent can be set close to each other, and the overall system size can be reduced. A similar effect can also be obtained when the reaction cuvette is rotated over 1 rotation minus 1 pitch in odd-numbered cycles.

In addition, with this embodiment, since the position of the reaction cuvette is shifted 1 pitch in odd-numbered cycles, a row of reaction cuvettes for which measurement cannot be performed because of passing the position for the measurement by the optical detector 51 in an accelerated or decelerated state are continued at successive timings. Those successive timings can be set in match with the timing of washing the reaction cuvette, which is in no way related to the measurement of the reaction process. It is therefore possible to continuously perform the analysis without including the timing at which the measurement is lacked during the reaction process, and to carry out the analysis on a variety of items ranging from an item requiring a short time reaction to an item requiring a long time reaction.

In another example of use, in the automatic analyzer having the same construction as that shown in FIGS. 1, 2 and 3, the reaction disk 36 is rotated clockwise in each stroke of 43 pitches per cycle. In this example, the reaction cuvette located at the position 1 on the reaction disk 36 is similarly moved to the position 2 on the reaction disk 36 in a next cycle. With this example, since the reaction cuvette passes the position of the optical detector 51 four times in 5 cycles, the number of measurements is increased and the analysis accuracy can be increased.

Figure 13:
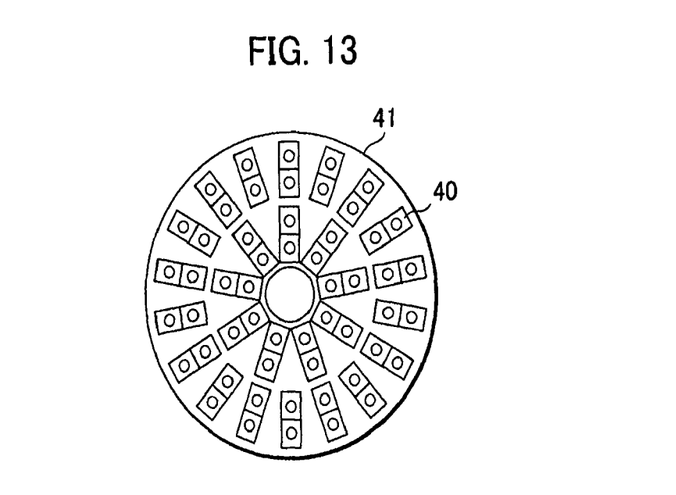
FIG. 13 is a schematic view showing the construction of a reagent disk in a second embodiment.

FIG. 13 shows a reagent disk according to a second embodiment of the present invention. In this second embodiment, reagent containers 40 are arranged on a reagent disk 41 in dual circumferential rows. Similarly, reagent containers 40 are arranged on a reagent disk 42 in dual circumferential rows. Since this embodiment enables a larger number of reagents to be arranged on a smaller reagent disk, the number of analyzable items can be increased without enlarging the overall system size.

Figure 14:
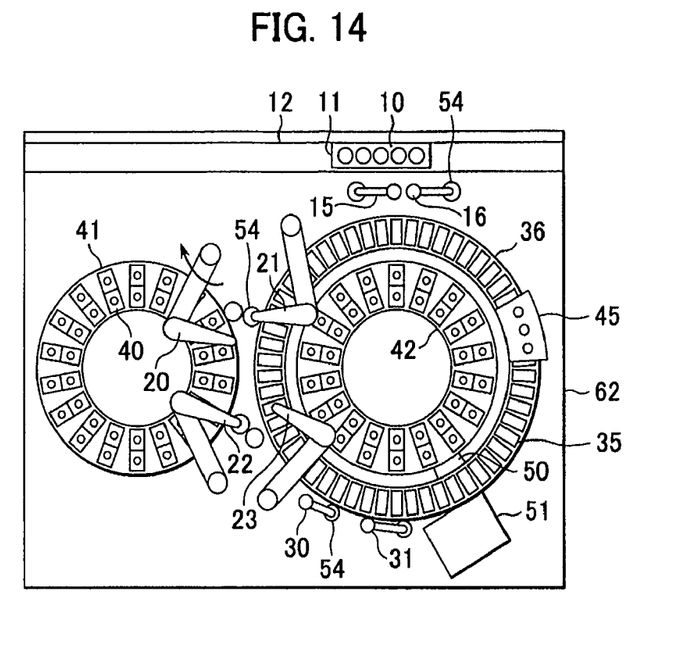
FIG. 14 is an explanatory view for explaining the operation of avoiding interference between the reagent dispensing probes.
Figure 15:
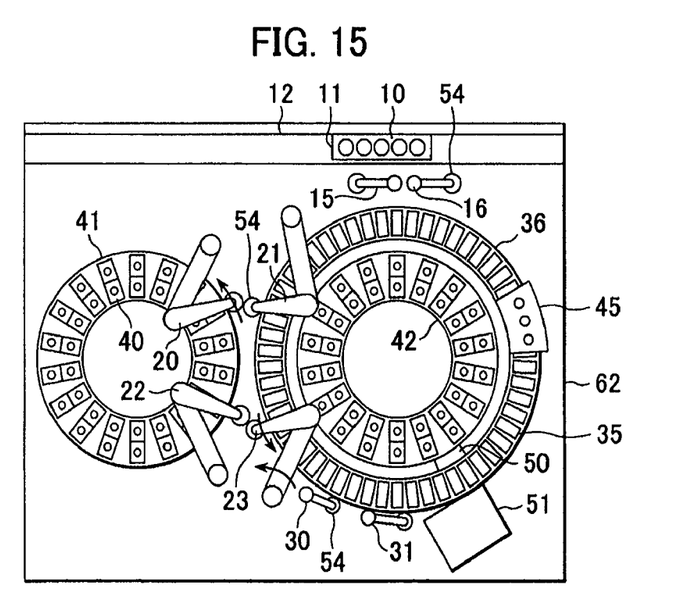
FIG. 15 is an explanatory view for explaining the operation of avoiding interference between the reagent dispensing probes.

One example of operation for avoiding interference between the reagent (dispensing) probes will be described below with reference to FIG. 12. In the state of FIG. 12, the reagent probe 20 ejects the first reagent to one corresponding reaction cuvette, and the reagent probe 23 ejects the second reagent to another corresponding reaction cuvette. In a next cycle, the reagent probe 20 and the reagent probe 23 are returned to respective washing ports 54 for washing of the reagent probes. The movement of each reagent probe to the washing port 54 is ideally performed by moving the first arm 74 and the second arm 79 at the same time for the purpose of minimizing the required time. However, because the reagent probe 21 is present near a path along which the reagent probe 20 is returned to the washing port 54, interference between those two reagent probes must be avoided. In such a case, only the first arm 74 of the reagent probe 20 is moved to a position where the second arm 79 does not interfere with the reagent probe 21 even when the second arm 79 is moved (FIG. 14). Then, the second arm 79 is moved for return to the washing port 54 (FIG. 15). On the other hand, there is no obstacle near a path along which the reagent probe 23 is returned to the washing port 54. Therefore, the reagent probe 23 can be returned to the washing port 54 by operating the first arm 74 and the second arm 79 at the same time (FIG. 15). As shown in this example, since the first arm 74 and the second arm 79 are operated independently of each other in the reagent probe of the present invention, the operation timing can be freely changed. Therefore, the path of the probe movement can be changed so as to avoid interference between the mechanism components, for example, when the reagent probes are moved to any points close to each other.

Further, shifting the operation timings of the first arm 74 and the second arm 79 gives rise to another effect of suppressing vibrations caused at a probe end. If the first arm 74 and the second arm 79 are operated to start at the same time and to stop at the same time, a vibration caused upon stop of the first arm 74 and a vibration caused upon stop of the second arm 79 are added to produce a larger vibration at the prove end when the probe is stopped. By operating the first arm 74 at earlier timing and operating the second arm 79 at later timing, for example, as in the above-mentioned example, only the second arm 79 is stopped and therefore the vibration caused at the prove end can be reduced at the time when the entire operation of the probe comes to an end. As a result, scattering of the reagent can be prevented.

What is claimed is:

1. An automatic analyzer comprising:
a plurality of reagent disks, with rotary axes of said reagent disks being different from each other;
a plurality of reagent containers being arranged along a circumference of each of said reagent disks;
a reaction disk on which a plurality of reaction cuvettes are arranged along a circumference;
a plurality of reagent dispensing probes arranged on each of said reagent disks, each of said reagent dispensing probes including a first arm rotatable about a first rotary shaft and a second arm rotatable about a second rotary shaft arranged on said first arm, said first arm and said second arm being rotatable independently of each other, each of said reagent dispensing probes movable to suck a reagent contained in said reagent containers and to eject the sucked reagent into a reaction cuvette, and where at least one pair of said plurality of reagent dispensing probes is arranged so that one reagent dispensing probe of said pair of reagent dispensing probes is disposed at one of said reagent disks and the other reagent dispensing probe of said pair of reagent dispensing probes is disposed at another of said reagent disks and is movable along a working path, and both dispensing probes are movable to eject the sucked reagents from the reagent containers on the reagent disks into the reaction cuvette at a same dispensing position on the reaction disk;
an optical detector to analyze reactions of said reagents and samples in said reaction cuvettes;
a washing port for washing the reagent dispensing probes; and
a controller configured to control each of the reagent dispensing probes, wherein when the second arm of the one reagent dispensing probe of said pair is to be moved to the washing port and interferes with the other reagent dispensing probe of said pair by obstructing the working path, the controller moves the first arm of the one reagent dispensing probe of said pair to a position where the second arm of the one reagent dispensing probe of said pair does not interfere with the other reagent dispensing probe of said pair, and thereafter, the controller moves the second arm of the one reagent dispensing probe of said pair to the washing port without interfering with the other reagent dispensing probe of said pair.

2. The automatic analyzer according to claim 1, wherein the controller is further configured to control each of the reagent dispensing probes arranged on each of said reagent disks so that only one of said reagent dispensing probes arranged on each of said reagent disks sucks the reagent during one cycle of a rotation of said reaction disk.

3. The automatic analyzer according to claim 1, wherein a sample and a plurality of said reagents are reacted in a reaction process in one reaction cuvette, a plurality of said reagents used for reaction in one reaction cuvette being arranged on a same reagent disk.

4. The automatic analyzer according to claim 1, further comprising a sample probe for dispensing a sample into said reaction cuvette,
wherein said automatic analyzer comprises a plurality of sets, each of which includes one set of said sample dispensing probe, a plurality of said reagent dispensing probes, and one of said reagent disks, and said automatic analyzer controls only any one set of said plurality of sets to be used for one analysis item.

5. The automatic analyzer according to claim 1, wherein at least one of said plurality of said reagent disks are arranged on an inner side of said reaction disk and a rotation axis of said at least one of said plurality of said reagent disks is a same axis of said reaction disk.

6. The automatic analyzer according to claim 1, wherein each of said reagent containers is one reagent container package containing a first reagent and a second reagent, both of which are used for analyzing a same analysis item, and each said reagent container package is exchangeable.

* * * * *